United States Patent [19]

Debono

[11] 4,399,067
[45] Aug. 16, 1983

[54] DERIVATIVES OF A-21978C CYCLIC PEPTIDES

[75] Inventor: Manuel Debono, Indianapolis, Ind.

[73] Assignee: Eli Lilly and Company, Indianapolis, Ind.

[21] Appl. No.: 380,498

[22] Filed: May 21, 1982

[51] Int. Cl.³ .......................................... C07C 103/52
[52] U.S. Cl. .......................................... 260/112.5 R
[58] Field of Search ............................... 260/112.5 R

[56] References Cited

U.S. PATENT DOCUMENTS

| | | | |
|---|---|---|---|
| 3,150,059 | 9/1964 | Kleinschmidt et al. | 260/112.5 R |
| 4,208,403 | 6/1980 | Hamill et al. | 424/115 |
| 4,289,692 | 9/1981 | Debono | 260/112.5 R |
| 4,293,482 | 10/1981 | Abbott et al. | 260/112.5 R |
| 4,293,484 | 10/1981 | Debono | 260/112.5 R |
| 4,293,486 | 10/1981 | Debono | 260/112.5 R |
| 4,293,489 | 10/1981 | Debono | 260/112.5 R |
| 4,297,277 | 10/1981 | Debono | 260/112.5 R |

FOREIGN PATENT DOCUMENTS 38-405867 7/1963 Japan ............................ 260/112.5 R

OTHER PUBLICATIONS

T. Kato et al., *J. Antibiotics* 29 (12) 1339–1340 (1976).
S. Chihara et al., *Agr. Biol. Chem.* 37 (11) 2455–2463 (1973).
S. Chihara et al., *ibid.* 37 (12) 2709–2717 (1973).
S. Chihara et al., *ibid.* 38 (3), 521–529 (1974).
S. Chihara et al., *ibid.* 38 (10) 1767–1777 (1974).
T. Suzuki et al., *J. Biochem.* 56 (4) 335–343 (1964).
J. M. Weber et al., *J. Antibiotics* 31 (4) 373–374 (1978).
J. Shoji et al., *ibid.* 28, 764–769 (1975).
J. Shoji et al., *ibid.* 29 (4) 380–389 (1976).
J. Shoji et al., *ibid.* 29 (12) 1268–1274 (1976).
J. Shoji et al., *ibid.* 29 (12) 1275–1280 (1976).

*Primary Examiner*—Delbert R. Phillips
*Attorney, Agent, or Firm*—Nancy J. Harrison; Arthur R. Whale

[57] ABSTRACT

A-21978C cyclic peptide derivatives of the formula

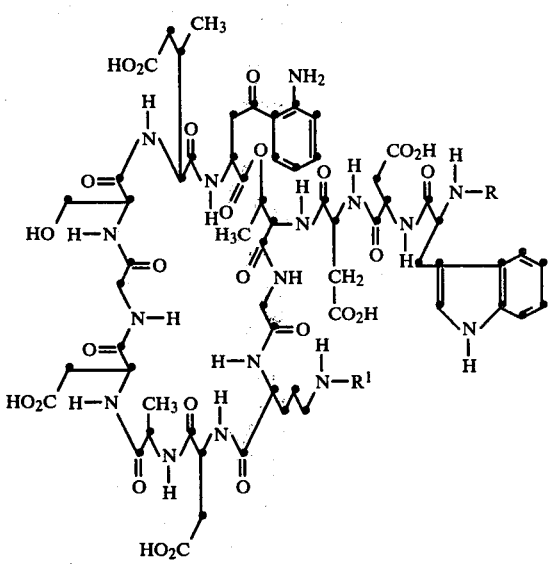

wherein R is a substituted benzoyl group of the formula

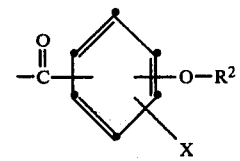

$R^2$ is $C_8$–$C_{15}$ alkyl; X is hydrogen, chloro, bromo, iodo, nitro, $C_1$–$C_3$ alkyl, hydroxy, $C_1$–$C_3$ alkoxy, or $C_1$–$C_3$ alkylthio; and $R^1$ is hydrogen or an amino-protecting group; and the salts thereof, are useful new semisynthetic antibacterial agents or intermediates to such agents.

8 Claims, No Drawings

DERIVATIVES OF A-21978C CYCLIC PEPTIDES

SUMMARY OF THE INVENTION

This invention relates to derivatives of A-21978C cyclic peptides which have formula 1:

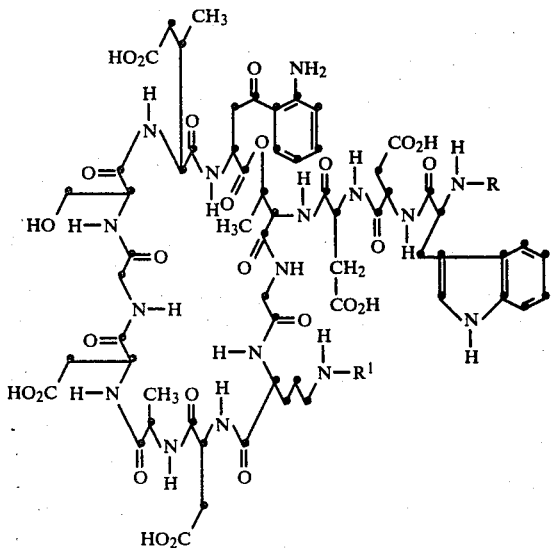

wherein R is a substituted benzoyl group of the formula

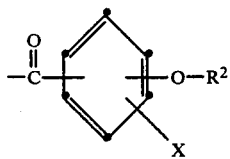

$R^2$ is $C_8$–$C_{15}$ alkyl; X is hydrogen, chloro, bromo, iodo, nitro, $C_1$–$C_3$ alkyl, hydroxy, $C_1$–$C_3$ alkoxy, or $C_1$–$C_3$ alkylthio; and $R^1$ is hydrogen or an amino-protecting group; and the salts of these petides. The A-21978C cyclic peptide derivatives and salts of this invention are useful semi-synthetic antibacterial agents or intermediates to such agents.

DETAILED DESCRIPTION OF THE INVENTION

In this specification the following abbreviations, most of which are commonly known in the art, are used:

| | |
|---|---|
| Ala: | alanine |
| Asp: | aspartic acid |
| Gly: | glycine |
| Kyn: | kynurenine |
| Orn: | ornithine |
| Ser: | serine |
| Thr: | threonine |
| Trp: | tryptophan |
| t-BOC: | tert-butoxycarbonyl |
| Cbz: | benzyloxycarbonyl |
| DMF: | dimethylformamide |
| THF: | tetrahydrofuran |
| HPLC: | high performance liquid chromatography |
| NMR: | $^1$H nuclear magnetic resonance |
| TLC: | thin-layer chromatography |
| UV: | ultraviolet |

FIELD OF THE INVENTION

Although there are many known antibacterial agents, the need for improved antibiotics continues. Antibiotics differ in their effectiveness against pathogenic organisms. Organism strains which are resistant to known antibiotics continually develop. In addition, individual patients often suffer serious reactions to specific antibiotics, due to hypersensitivity and/or to toxic effects. There is, therefore, a continuing need for new and improved antibiotics.

THE PRIOR ART

The A-21978C antibiotics are closely related, acidic peptide antibiotics. Members of this class of antibiotics which were previously known include crystallomycin, amphomycin, zaomycin, aspartocin, and glumamycin [see T. Korzybski, Z. Kowszyk-Gindifer and W. Kurylowicz, "Antibiotics-Origin, Nature and Properties," Vol. I, Pergamon Press, New York, N.Y., 1967, pp. 397–401 and 404–408]; tsushimycin [J. Shoji, et al., J. Antibiotics 21, 439–443 (1968)]; laspartomycin [H. Naganawa, et al., J. Antibiotics 21, 55–62 (1968)]; brevistin [J. Shoji and T. Kato, J. Antibiotics 29, 380–389 (1976)]; cerexin A [J. Shoji, et al., J. Antibiotics 29, 1268–1274 (1976)] and cerexin B [J. Shoji and T. Kato, J. Antibiotics 29, 1275–1280 (1976)]. Of these antibiotics, brevistin, cerexin A and cerexin B appear to be most closely related to the A-21978C antibiotics.

The A-21978C antibiotics are described by Robert L. Hamill and Marvin M. Hoehn in U.S. Pat. No. 4,208,403, issued June 17, 1980, which is incorporated herein by reference. As described in U.S. Pat. No. 4,208,403, the A-21978 antibiotic complex contains a major component, factor C, which is itself a complex of closely related factors. A-21978 factor C, which is called the A-21978C complex, contains individual factors $C_0$, $C_1$, $C_2$, $C_3$, $C_4$ and $C_5$. Factors $C_1$, $C_2$ and $C_3$ are major factors; and factors $C_0$, $C_4$ and $C_5$ are minor factors. The structure of the A-21978C factors is shown in formula 2:

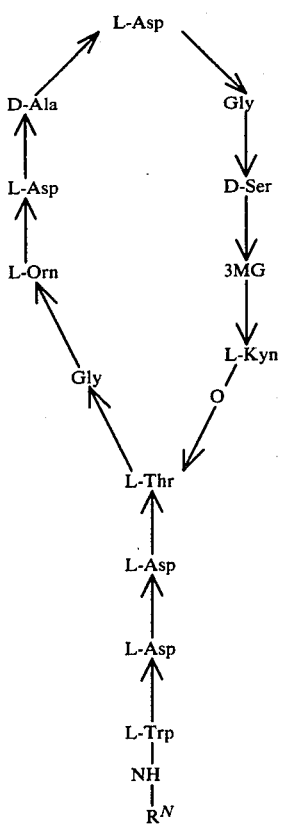

wherein 3MG represents L-threo-3-methylglutamic acid, and $R^N$ represents a specific fatty acid moiety. The specific $R^N$ groups of the factors are as follows:

| A-21978C Factor | $R^N$ Moiety |
|---|---|
| $C_1$ | 8-methyldecanoyl |
| $C_2$ | 10-methylundecanoyl |
| $C_3$ | 10-methyldodecanoyl |
| $C_0$ | $C_{10}$—alkanoyl* |
| $C_4$ | $C_{12}$—alkanoyl* |
| $C_5$ | $C_{12}$—alkanoyl* |

*Identity not yet determined

Kleinschmidt et al. in U.S. Pat. No. 3,150,059, issued in 1964, described an enzyme elaborated by the Actinoplanaceae which was capable of deacylating penicillin antibiotics. Abbott and Fukuda in U.S. Pat. Nos. 4,293,482, 4,299,764, 4,299,762, 4,304,716, and 4,293,490, all issued in 1981, reported that an Actinoplanaceae enzyme was capable of deacylating the A-30912 type of cyclic peptide antibiotic. Reacylation of the A-30912 nucleus to form useful antifungal compounds was reported by Abbott and Fukuda in U.S. Pat. No. 4,287,120, issued in 1981, and in U.S. Pat. Nos. 4,320,052, 4,320,053, 4,320,054 and 4,322,338, issued in 1982; and by Debono in the following U.S. Patents issued in 1981; U.S. Pat. Nos. 4,293,483, 4,293,488, 4,293,487, 4,293,485, 4,293,491, 4,293,489, 4,297,277, 4,289,692, 4,293,486 and 4,293,484.

In 1967 Kimura and Tatsuki, in Japanese Patent 4058/67 (Derwent Abstr. 26695), described the enzymatic deacylation of the peptide antibiotic glumamycin. The microorganism catalyzing the deacylation was identified as closely related to *Pseudomonas dacunhae*. They stated that "decylated derivatives of the compounds are useful as the matrial for synthesis of the related compounds, as in the case of 6-aminopenicillanic acid for penicillin", but gave no examples of re-acylation.

In 1965, Kimura and coworkers reported that a bacterium isolated from soil catalyzed the deacylation of the peptide antibiotic colistin (polymyxin E) (see Kimura, et al., Abstracts of Papers, 21st Meeting of the Pharmaceutical Society of Japan, Tokushima, Oct. 1965, p. 422). They reported that new derivatives of colistin were prepared by acylation of the deacylated nucleus, but did not discuss whether these derivatives had any activity.

Kato and Shoji [*J. Antibiotics* 29 (12), 1339-1340 (1976)] attempted to use the enzyme described by Kimura et al. to deacylate the cyclic peptide antibiotic octapeptin $C_1$. The enzyme did not catalyze the desired reaction. It was subsequently found that deacylation could be accomplished chemically by oxidation of the β-hydroxyl group of the fatty acid followed by treatment with hydroxylamine.

In 1973 Chihara and coworkers reported their work with colistin. In this work two plant proteases, ficin and papain, were used to hydrolyze colistin to a nonapeptide and a fatty acyl α,γ-diaminobutyric acid residue. The plant enzymes, however, in addition to removing the fatty acid acyl substituent, also removed the terminal amino acid of the colistin molecule [See S. Chihara et al., *Agr. Biol. Chem.* 37 (11), 2455-2463 (1973); ibid. 37 (12), 2709-2717 (1973); ibid. 38 (3), 521-529 (1974); and ibid. 38 (10), 1767-1777 (1974)]. The colistin nonapeptide was isolated and then reacylated with a variety of fatty acid chlorides. Subsequently, Chihara's group produced N-fatty acyl mono-acyl derivatives of colistin nonapeptide. These derivatives restored a tenth amino acid to the colistin nonapeptide and were used to study structure-activity relationships.

The polymyxin antibiotics have been hydrolyzed with the enzyme subtilopeptidase A [See T. Suzuki et al., *J. Biochem.* 56 (4), 335-343 (1964)]. This enzyme deacylated the peptides, but in addition hydrolyzed some of the peptide bonds so that a variety of peptide products resulted.

In 1978 Weber and Perlman reported that a Corynebacterium isolated from soil inactivated the peptide antibiotic amphomycin by deacylation of the isotridecanoic acid side chain [see *J. Antibiotics* 31 (4), 373-374 (1978)].

Kuwana et al. in U.S. Pat. No. 4,050,989, issued in 1977, described the deacylation of pepsin-inhibiting peptides (pepsidines) by an enzyme from *Bacillus pumilus* and the use of these products to prepare N-acyl-pentapeptide homologs.

Shoji and coworkers deacylated the cyclic peptide antibiotics cerexin A, cerexin B, and brevistin in order to determine the structures of these antibiotics [see J. Shoji and T. Kato, *J. Antiobiotics* 28, 764-769 (1975) and ibid. 29 (4), 380-389 (1976); and J. Shoji et al., ibid. 29 (12), 1268-1274 (1976); and ibid. 29 (12), 1275-1280 (1976)]. Deacylation was accomplished with an enzyme preparation prepared from Pseudomonas sp. M-6-3 (polymyxin acylase) and by chemical means. Chemical deacylation, however, resulted in extensive side reactions.

Despite the contributions of these groups, it is extremely difficult, when confronted with the problem of deacylating a peptide antibiotic having a different structure, to know whether an enzyme exists which can be used for this purpose. Finding such an enzyme is even more difficult when the substrate antibiotic contains a cyclic peptide nucleus. Enzymes have a high degree of specificity. Differences in the peptide moiety and in the side chain of the substrate antibiotic will affect the outcome of the deacylation attempt. In addition, many microorganisms make a large number of peptidases which attack different portions of the peptide moiety. This frequently leads to intractable mixtures of products.

Thus, it was most surprising that what may be the same enzyme which was used to deacylate penicillins and the A-30912 antibiotics could also be used successfully to deacylate the A-21978C antibiotics. In each of the A-21978C antibiotics (formula 2), the fatty acid side chain ($R^N$) is attached at the α-amino group of the tryptophan residue. In a co-pending application of Abbott, Debono and Fukuda, entitled "A-21978C CYCLIC PEPTIDES", Ser. No. 380,497, filed herewith this even date, the full disclosure of which is incorporated herein by reference, is described the discovery that the fatty acid side chain can be cleaved by an enzyme without affecting the chemical integrity of the remainder of the A-21978C peptide.

The enzyme used to effect the deacylation reaction is produced by a microorganism of the family Actinoplanaceae, preferably the microorganism *Actinoplanes utahensis* NRRL 12052, or a variant thereof. To accomplish deacylation, an antibiotic selected from A-21978C complex, A-21978C factors, $C_0$, $C_1$, $C_2$, $C_3$, $C_4$, and $C_5$, blocked A-21978C complex, and blocked A-21978C factors $C_0$, $C_1$, $C_2$, $C_3$, $C_4$, and $C_5$ is added to a culture of the microorganism. The terms "blocked A-21978C factors" and "blocked A-21978C complex" refer to individual A-21978C factors or mixtures of factors (complex) wherein an amino-protecting group is located on the δ-amino group of ornithine of the individual factor or mixture of factors. The culture is allowed to incubate with the substrate until the deacylation is substantially complete. The corresponding A-21978C cyclic peptide thereby obtained is separated from the fermentation broth by methods known in the art.

The cyclic peptides obtained by these enzymatic deacylations are shown in formula 3.

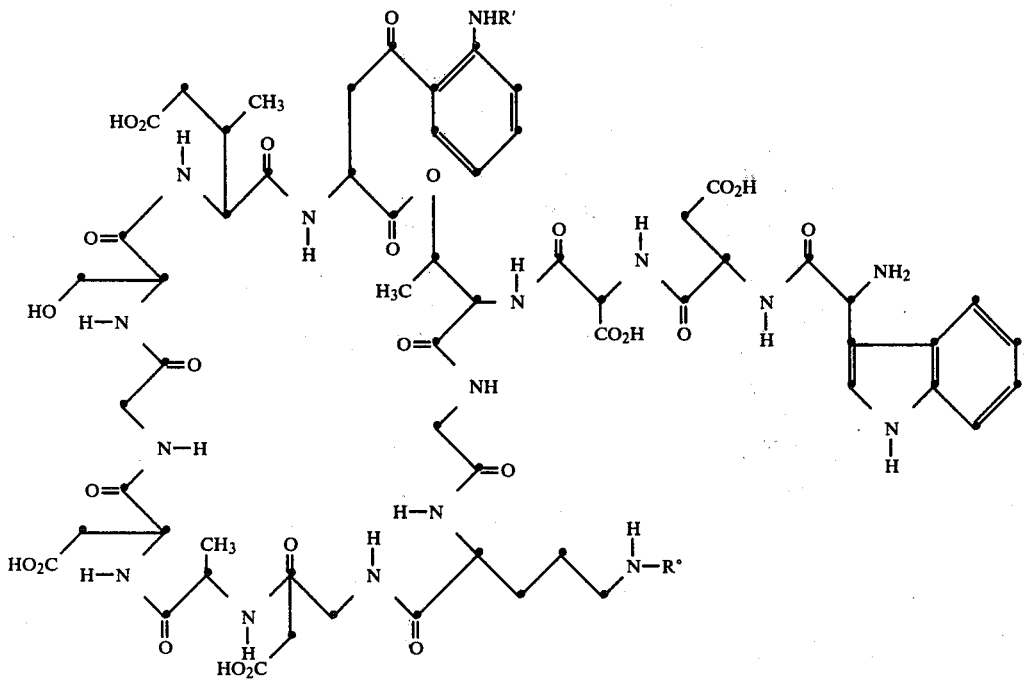

3 wherein R' and $R^o$ are, independently, hydrogen or an amino-protecting group; and the salts thereof.

Removal of the acyl moiety from the A-21978C complex or A-21978C individual factors $C_0$, $C_1$, $C_2$, $C_3$, $C_4$, and $C_5$ gives the compound of formula 3 wherein $R^o$ and R' each represent hydrogen, which is the common cyclic peptide present in antibiotic A-21978C factors. For convenience herein, this compound will be called A-21978C nucleus. This compound can also be represented by formula 4:

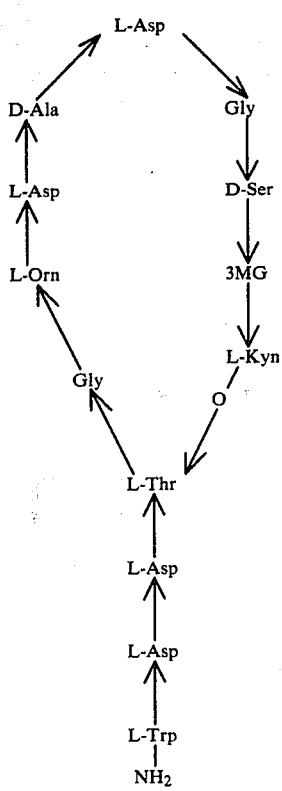

wherein 3MG represents L-threo-3-methylglutamic acid.

The compounds of formula 3 wherein R⁰ R' are other than hydrogen are prepared by deacylation of appropriately blocked antibiotic A-21978C factors $C_0$, $C_1$, $C_2$, $C_3$, $C_4$ and $C_5$. For convenience herein these compounds will be called blocked A-21978C nuclei. These blocked compounds are useful intermediates to certain peptides of formula 1, i.e. those compounds wherein $R^1$ is an amino-protecting group.

As will be apparent to those skilled in the art, A-21978C nucleus and blocked A-21978C nuclei can be obtained either in the form of free amines or of acid addition salts. Although any suitable acid addition salt may be used, those which are non-toxic and pharmaceutically acceptable are preferred.

The method of preparing the A-21978C nuclei of formula 3 from the corresponding A-21978C antibiotic by means of fermentation using Actinoplanes utahensis NRRL 12052 is described in co-pending application of Abbott et al., Ser. No. 380,497. A. utahensis NRRL 12052 is available to the public from the Agricultural Research Culture Collection (NRRL), Northern Regional Research Center, U.S. Department of Agriculture, 1815 North University St., Peoria, Ill. 61604, U.S.A., under the accession number NRRL 12052. Preparation 1 herein illustrates the preparation of A-21978C nucleus by fermentation using the A-21978C complex as the substrate and *Actinoplanes utahensis* NRRL 12052 as the microorganism.

Other Actinoplanaceae cultures which can be used to prepare the A-21978C nuclei of formula 3 are available to the public from the Northern Regional Research Laboratory under the following accession numbers:

| | |
|---|---|
| *Actinoplanes missouriensis* | NRRL 12053 |
| *Actinoplanes* sp. | NRRL 8122 |
| *Actinoplanes* sp. | NRRL 12065 |
| *Streptosporangium roseum* var. *hollandensis* | NRRL 12064 |

The effectiveness of any given strain of microorganism within the family Actinoplanaceae for carrying out the deacylation is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a Micrococcus luteus assay. Loss of antibiotic activity is an indication that the microorganism produces the requisite enzyme for deacylation. This must be verified, however, using one of the following methods: (1) analysis by HPLC for presence of the intact nucleus; or (2) re-acylation with an appropriate side chain (e.g. lauroyl, n-decanoyl or n-dodecanoyl) to restore activity.

The present invention relates to novel compounds derived by acylating an A-21978C nucleus (compound of formula 3). The compounds of the present invention have the chemical structure depicted in formula 1:

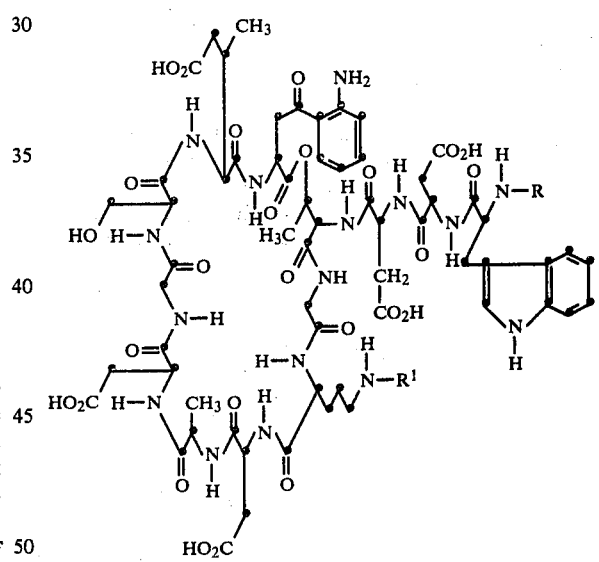

wherein R is a substituted benzoyl group of the formula

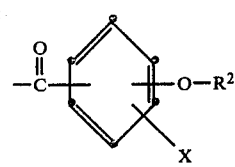

$R^2$ is $C_8-C_{15}$ alkyl; X is hydrogen, chloro, bromo, iodo, nitro, $C_1-C_3$ alkyl, hydroxy, $C_1-C_3$ alkoxy, or $C_1-C_3$ alkylthio; and $R^1$ is hydrogen or an amino-protecting group; and the salts thereof.

It will be recognized by those skilled in the art that in the substituted benzoyl group, the

function and the —OR² function may be oriented on the benzene ring in the ortho, meta, or para position relative to each other. The para orientation for these groups is preferred. The substituent represented by X may be substituted at any available position of the benzene ring not occupied by these two groups.

As used herein, the term "alkyl" comprehends both straight and branched hydrocarbon chains.

The term "amino-protecting group" refers to a recognized amino-protecting group which is compatible with the other functional groups in the A-21978C molecule. Preferably, amino-protecting groups are those which can be readily removed from the subsequently acylated compound. Examples of suitable protecting groups can be found in "Protective Groups in Organic Synthesis" by Theodora W. Greene, John Wiley and Sons, New York, 1981, Chapter 7. Especially preferable amino-protecting groups are the tert-butoxycarbonyl and benzyloxycarbonyl groups.

Illustrative $C_8$-$C_{15}$ alkyl radicals which are preferred for $R^2$ for the purposes of this invention are:

(a) —$(CH_2)_nCH_3$ wherein n is an integer from 7 to 14; and (b)

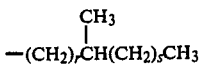

wherein r and s are, independently, an integer from 0 to 12, provided that r+s can be no greater than 12 or no less than 5.

The compounds of formula 1 are capable of forming salts. These salts are also part of this invention. Such salts are useful, for example, for separating and purifying the compounds. Pharmaceutically-acceptable alkali-metal, alkaline-earth-metal, amine and acid-addition salts are particularly useful.

For example, the compounds of formula 1 have five free carboxyl groups which can form salts. Partial, mixed and complete salts of these carboxyl groups are, therefore, contemplated as part of this invention. In preparing these salts, pH levels greater than 10 should be avoided due to the instability of the compounds at such levels.

Representative and suitable alkali-metal and alkaline-earth metal salts of the compounds of formula 1 include the sodium, potassium, lithium, cesium, rubidium, barium, calcium and magnesium salts. Suitable amine salts of the formula 1 compounds include the ammonium and the primary, secondary, and tertiary $C_1$-$C_4$-alkylammonium and hydroxy-$C_2$-$C_4$-alkylammonium salts. Illustrative amine salts include those formed by reaction of a formula 1 compound with ammonium hydroxide, methylamine, sec-butylamine, isopropylamine, diethylamine, di-isopropylamine, cyclohexylamine, ethanolamine, triethylamine, 3-amino-1-propanol, and the like.

The alkali-metal and alkaline-earth-metal cationic salts of the compounds of formula 1 are prepared according to procedures commonly used for the preparation of cationic salts. For example, the free acid form of a formula 1 compound is dissolved in a suitable solvent such as warm methanol or ethanol; a solution containing the stoichiometric quantity of the desired inorganic base in aqueous methanol is added to this solution. The salt thus formed can be isolated by routine methods, such as filtration or evaporation of the solvent.

The salts formed with organic amines can be prepared in a similar manner. For example, the gaseous or liquid amine can be added to a solution of a formula 1 compound in a suitable solvent such as ethanol; the solvent and excess amine can be removed by evaporation.

The compounds of this invention also have free amino groups and can, therefore, form acid addition salts. Such salts are also part of this invention. Representative and suitable acid-addition salts of the compounds of formula 1 include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicylic, methanesulfonic, benzenesulfonic, sorbic, picric, benzoic, cinnamic, and like acids.

The componds of formula 1 are prepared by acylating a compound of formula 3, using methods conventional in the art for forming an amide bond. The acylation is accomplished, in general, by reacting the selected compound with an activated derivative of the substituted benzoic acid (formula 5) corresponding to the desired acyl group (R):

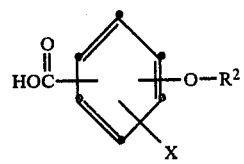

(X and $R^2$ have the meanings described supra).

Illustrative compounds of formula 5 include the following: p-(n-octyloxy)benzoic acid, p-(n-decyloxy)benzoic acid, p-(n-dodecyloxy)benzoic acid, p-(n-pentadecyloxy)benzoic acid, m-chloro-p-(n-dodecyloxy)-benzoic acid, p-chloro-m-(n-decyloxy)benzoic acid, m-(n-dodecyloxy)-p-methylbenzoic acid, m-methoxy-p-(n-octyloxy)benzoic acid and m-hydroxy-p-(n-pentyloxy)-benzoic acid.

The term "activated derivative" means a derivative which renders the carboxyl function of the acylating agent reactive to coupling with the primary amino group to form the amide bond which links the side chain to the nucleus. Suitable activated derivatives, their methods of preparation, and their methods of use as acylating agents for a primary amine will be recognized by those skilled in the art. Preferred activated derivatives are: (a) an acid halide (e.g. an acid chloride), (b) an acid anhydride (e.g. an alkoxyformic acid anhydride or aryloxyformic acid anhydride) or (c) an activated ester (e.g. a 2,4,5-trichlorophenyl ester, an N-hydroxybenztriazole ester, or an N-hydroxysuccinimide ester). Other methods for activating the carboxyl function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

It will be recognized by those skilled in the art that the compounds of formula 1 are prepared using selective acylation procedures and with the assistance of amino-protecting groups. For example, when a compound of formula 3 wherein R' and R⁰ are hydrogen is the starting material, acylation can occur at both the α-amino group of tryptophan and the δ-amino group of ornithine to give $N_{Trp}$, $N_{Orn}$-diacyl derivatives. To obtain derivatives monoacylated at the α-amino group of tryptophan, therefore, it is preferable to acylate a compound of formula 3 wherein the δ-amino group of ornithine (the R⁰ position) is blocked by an amino-protecting group. Such starting materials are preferably obtained by blocking the A-21978C factor at this position before it is deacylated. The aromatic amino group of kynurenine (the R' position in formula 3) is the least reactive of the three free amino groups in the A-21978C nucleus. Thus, acylation at the R position of formula 1 does not usually involve blocking of the kynurenine amino group.

Scheme I outlines general procedures for the preparation of the compounds of formula 1. In this Scheme the following symbols are used:

```
[*]   = remainder of A-21978C
N_T   = α-amino group or tryptophan
N_O   = δ-amino group of ornithine
N_K   = aromatic amino group of kynurenine
R     = formula 1 substituents as defined
R_N   = acyl group of natural factor
B     = amino-protecting group
Acyl  = an acylation step
Deacyl = a deacylation step
Block = acylation with an amino-protecting group
Deblock = removal of an amino-protecting group
```

In Scheme I the $N_{Trp}$-monoacyl derivatives of A-21978C are represented by general formula 3.

Scheme I: Preparation of $N_{Trp}$—Monoacyl-A21978C Derivatives

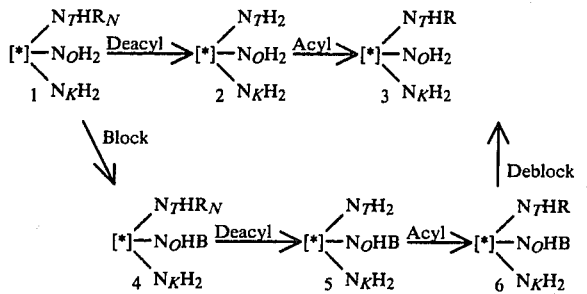

A preferred method for preparing the compounds of formula 1 is by the active ester method. The use of the 2,4,5-trichlorophenyl ester of the desired side chain acid (formula 5) as the acylating agent is most preferred. In this method, an excess amount of the active ester is reacted with the nucleus at room temperature in a nonreactive organic solvent such as DMF, THF, diethyl ether or dichloromethane. The reaction time is not critical, although a time of about 24 to about 120 hours is preferred. At the conclusion of the reaction, the solvent is removed, and the residue is purified by chromatography, such as reversed phase HPLC using silica gel $C_{18}$ reversed phase resin as the stationary phase and a mixture of $H_2O/CH_3OH/CH_3CN$ as the solvent system.

The 2,4,5-trichlorophenyl esters are conveniently made by treating the side chain acid (formula 5) with 2,4,5-trichlorophenol in the presence of a coupling agent, such as N,N'-dicyclohexylcarbodiimide. Other methods of preparation of the active esters will be apparent to those skilled in the art.

The substituted acids of formula 5, and the activated derivatives thereof, are either known compounds or they can be made from known compounds by methods known in the art. The alkoxybenzoic acids can be prepared conveniently from an appropriate hydroxybenzoic acid by reacting an appropriate alkyl halide with the disodium salt of the appropriate hydroxybenzoic acid. The hydroxybenoic acids and substituted derivatives thereof used as starting material in the processes described herein are either known compounds or can be prepared by conventional methods which are known in the art.

When an A-21978C cyclic peptide of this invention is used as an antibacterial agent, it may be administered either orally or parenterally. As will be appreciated by those skilled in the art, the A-21978C compound is commonly administered together with a pharmaceutically acceptable carrier or diluent.

The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose may be added to make the solutions isotonic. The proportions and nature of such additives will be apparent to those skilled in the art.

For oral use, the compounds can be administered in combination with pharmaceutically acceptable carriers or excipients in the form of capsules, tablets or powders. The nature and proportion of such carriers or excipients will be recognized by those skilled in the art.

The dosage of A-21978C compound will depend upon a variety of considerations, such as, for example, the particular compound being used and the nature and severity of the infection to be treated. Those skilled in the art will recognize that appropriate dosage ranges and/or dosage units for administration may be determined by considering the MIC and $ED_{50}$ values and toxicity data herein provided together with factors such as pharmacokinetics, the patient or host and the infecting microorganism.

The methods of making and using the compounds of the present invention are illustrated in the following examples:

PREPARATION 1

Preparation of A-21978C Nucleus

A. Fermentation of *Actinoplanes utahensis*

A stock culture of *Actinoplanes utahensis* NRRL 12052 is prepared and maintained on an agar slant. The medium used to prepare the slant is selected from one of the following:

| MEDIUM A | |
|---|---|
| Ingredient | Amount |
| Pre-cooked oatmeal | 60.0 g |
| Yeast | 2.5 g |
| $K_2HPO_4$ | 1.0 g |
| Czapek's mineral stock* | 5.0 ml |
| Agar | 25.0 g |
| Deionized water | q.s. to 1 liter | pH before autoclaving is about 5.9; adjust to pH 7.2 by addition of NaOH; after autoclaving, pH is about 6.7.
*Czapek's mineral stock has the following composition:
  $FeSO_4.7H_2O$ (dissolved in  2 g -continued

| MEDIUM A | |
|---|---|
| Ingredient | Amount |
| 2 ml conc HCl) | |
| KCl | 100 g |
| MgSO$_4$.7H$_2$O | 100 g |
| Deionized water | q.s. to 1 liter |

| MEDIUM B | |
|---|---|
| Ingredient | Amount |
| Potato dextrin | 5.0 g |
| Yeast extract | 0.5 g |
| Enzymatic hydrolysate of casein* | 3.0 g |
| Beef extract | 0.5 g |
| Glucose | 12.5 g |
| Corn starch | 5.0 g |
| Meat peptone | 5.0 g |
| Blackstrap molasses | 2.5 g |
| MgSO$_4$.7H$_2$O | 0.25 g |
| CaCO$_3$ | 1.0 g |
| Czapek's mineral stock | 2.0 ml |
| Agar | 20.0 g |
| Deionized water | q.s. to 1 liter |

*N—Z—Amine A, Humko Sheffield Chemical, Lyndhurst, NJ.

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
|---|---|
| Pre-cooked oatmeal | 20.0 g |
| Sucrose | 20.0 g |
| Yeast | 2.5 g |
| Distiller's Dried Grain* | 5.0 g |
| K$_2$HPO$_4$ | 1.0 g |
| Czapek's mineral stock | 5.0 ml |
| Deionized water | q.s. to 1 liter |

Adjust to pH 7.4 with NaOH; after autoclaving, pH is about 6.8.
*National Distillers Products Co., 99 Park Ave., New York, NY.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen," *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (80 ml), prepared as above-described, is used to inoculate 10 liters of sterile production medium selected from one of the following:

| MEDIUM I | |
|---|---|
| Ingredient | Amount (g/L) |
| Peanut meal | 10.0 |
| Soluble meat peptone | 5.0 |
| Sucrose | 20.0 |
| KH$_2$PO$_4$ | 0.5 |
| K$_2$HPO$_4$ | 1.2 |
| MgSO$_4$.7H$_2$O | 0.25 |
| Tap water | q.s. to 1 liter |

The pH of the medium is about 6.9 after sterilization by autoclaving at 121° C. for 45 minutes at about 16–18 psi.

| MEDIUM II | |
|---|---|
| Ingredient | Amount (g/L) |
| Sucrose | 30.0 |
| Peptone | 5.0 |
| K$_2$HPO$_4$ | 1.0 |
| KCl | 0.5 |
| MgSO$_4$.7H$_2$O | 0.5 |
| FeSO$_4$.7H$_2$O | 0.002 |
| Deionized water | q.s. to 1 liter |

Adjust to pH 7.0 with HCl; after autoclaving, pH is about 7.0.

| MEDIUM III | |
|---|---|
| Ingredient | Amount (g/L) |
| Glucose | 20.0 |
| NH$_4$Cl | 3.0 |
| Na$_2$SO$_4$ | 2.0 |
| ZnCl$_2$ | 0.019 |
| MgCl$_2$.6H$_2$O | 0.304 |
| FeCl$_3$.6H$_2$O | 0.062 |
| MnCl$_2$.4H$_2$O | 0.035 |
| CuCl$_2$.2H$_2$O | 0.005 |
| CaCO$_3$ | 6.0 |
| KH$_2$PO$_4$* | 0.67 |
| Tap water | q.s to 1 liter |

*Sterilized separately and added aseptically
Final pH about 6.6.

The inoculated production medium is allowed to ferment in a 14-liter fermentation vessel at a temperature of about 30° C. for about 66 hours. The fermentation medium is stirred with conventional agitators at about 600 RPM and aerated with sterile air to maintain the dissolved oxygen level above 30% of air saturation at atmospheric pressure.

B. Deacylation of A-21978C

A fermentation of *A. utahensis* is carried out as described in Section A, using slant medium A and production medium I and incubating the production medium for about 67 hours. Crude A-21978C complex (100 g), prepared as described in U.S. Pat. No. 4,208,403, is added to the fermentation medium.

Deacylation of the A-21978C complex is monitored by assay against *Micrococcus luteus*. The fermentation is allowed to continue until deacylation is complete as indicated by disappearance of activity vs. *M. luteus*, a period of about 24 hours.

C. Isolation of A-21978c Nucleus

Whole fermentation broth (20 liters), obtained as described in Section B, was filtered with a filter aid (Hyflo Super-Cel, Johns Manville Corp.). The mycelial cake was discarded. The filtrate thus obtained was passed through a column containing 1.5 liters of HP-20 resin (DIAION High Porous Polymer, HP-Series, Mitsubishi Chemical Industries Limited, Tokyo, Japan). The effluent thus obtained was discarded. The column was then washed with deionized water (10 L.) to remove residual filtered broth. This wash water was discarded. The column was then eluted with water-:acetonitrile mixtures (10 L. each of 95:5, 9:1, and 4:1), collecting 1-liter fractions.

Elution was monitored by paper chromatography, using an n-butanol:pyridine:acetic acid:water (15:10:3:12) solvent system and detecting compounds by UV fluorescence. In this system the A21978C factors have an $R_f$ value of about 0.56 and A-21978C nucleus has an $R_f$ value of about 0.32. The product can also be checked by analytical HPLC, using silica gel/$C_{18}$ and a solvent system of water:methanol (3:1) containing 0.1% ammonium acetate, detecting the nucleus with a UV monitor at 254 nm.

Fractions containing the nucleus were combined, concentrated under vacuum to remove the acetonitrile and freeze-dried to give 40.6 g of semi-purified A-21978C nucleus.

D. Purification of A-21978C Nucleus

Semi-purified A-21978C nucleus (15 g), obtained as described in Section C, was dissolved in 75 ml of water:-methanol:acetonitrile (82:10:8) containing 0.2% acetic acid and 0.8% pyridine. This solution was pumped onto a 4.7-×192-cm column containing 3.33 L. of silica gel/$C_{18}$ (Quantum LP-1, Quantum Industries, 341 Kaplan Drive, Fairfield, N.J. 07006). The column was developed with the same solvent system. Fractions having a volume of 350 ml were collected. Separation was monitored at 280 nm with a UV monitor. Fractions containing the nucleus were combined, concentrated under vacuum to remove solvents and freeze-dried to give 5.2 g of purified A-21978C nucleus.

E. Characteristics of A-21978C Nucleus

A-21978C nucleus has the following characteristics:

(a) Form: white amorphous solid which fluoresces under short-wave UV (b) Empirical formula: $C_{62}H_{82}N_{16}O_{26}$ (c) Molecular weight: 1466

(d) Solubility: soluble in water (e) Infrared absorption spectrum (KBr disc) shows absorption maxima at:
 3300 (broad), 3042 (weak), 2909 (weak), 1655 (strong), 1530 (strong), 1451 (weak), 1399 (medium), 1222 (medium), 1165 (weak), 1063 (weak) and 758 (medium to weak)

(f) UV absorption spectrum in methanol shows maxima at 223 nm ($\epsilon$ 41,482) and 260 nm ($\epsilon$ 8,687)

(g) Electrometric titration in 66% aqueous dimethylformamide indicates the presence of four titratable groups with p$K_a$ values of about 5.2, 6.7, 8.5 and 11.1 (initial pH 6.12).

PREPARATION 2

Alternate Preparation of A-21978C Nucleus

A-21978C nucleus was prepared according to the method of Preparation 1 except for certain changes in Section B. The *A. utahensis* culture was incubated initially for about 48 hours; the substrate was semipurified A-21978C complex (50 g); and incubation after addition of the substrate was about 16 hours. The broth filtrate was passed over a column containing 3.1 liters of HP-20 resin. The column was washed with 10 volumes of water and then was eluted with water:acetonitrile (95:5). Elution was monitored as in Preparation 1. After collecting 24 liters, the eluting solvent was changed to water:acetonitrile (9:1). Fractions containing the nucleus were eluted with this solvent. These fractions were combined, concentrated under vacuum to remove acetonitrile, and freeze-dried to give 24.3 g of semi-purified A-21978C nucleus.

This semi-purified A-21978C nucleus (24.3 g) was dissolved in water (400 ml). The solution was pumped onto a 4.7-×192-cm steel column containing 3.33 liters of silica gel (Quantum LP-1)/$C_{18}$ prepared in water:methanol:acetonitrile (8:1:1) containing 0.2% acetic acid and 0.8% pyridine. The column was developed with the same solvent at a pressure of about 2000 psi, collecting 350 ml fractions. Elution was monitored by UV at 280 nm. Fractions containing the nucleus were combined, concentrated under vacuum to remove solvents, and freeze-dried to give 14 g of highly purified A-21978C nucleus.

PREPARATION 3

Preparation of $N_{Orn}$-t-BOC A-21978C Factors $C_2$ and $C_3$

A mixture of A-21978C factors $C_2$ and $C_3$ (10 g), prepared as described in U.S. Pat. No. 4,208,403, was dissolved in water (50 ml) with sonication (200 mg/ml). The pH of the solution was adjusted from 4.05 to 9.5 with 5 N NaOH (3.6 ml). Di-tert-butyl dicarbonate (3.0 ml) was added, and the reaction mixture was stirred at room temperature for 2 hours. The pH of the reaction was maintained at 9.5 by manual addition of 5 N NaOH (6.5 ml added in 2 hours).

The reaction was monitored periodically by TLC on silica gel, using $CH_3CN:H_2O$ (7:3 and 8:2) solvent systems and detecting by UV.

After about 10 minutes the reaction solution became rapidly turbid, and base consumption increased. After 30 minutes, the rate of increase in turbidity and the rate of base consumption decreased, indicating that the reaction was complete. Nevertheless, the reaction was continued for an additional 90 minutes to insure completion. At the end of the two-hour reaction, the reaction material was lyophilized immediately to give 12.7 g of $N_{Orn}$-t-BOC-A-21978 factors $C_2$ and $C_3$.

Using similar procedures, two 10-g reactions and a 30-g reaction were run. In each of these the reaction time was only 40 minutes. The two 10-g experiments gave 11.9 and 12.1 g of product, respectively. The 30-g reaction gave 35.4 g of product.

PREPARATION 4

Preparation of A-21978C $N_{Orn}$-t-BOC Nucleus

A. Fermentation of *A. utahensis*

A fermentation of *A. utahensis* was carried out as described in Preparation 1, Section A, using slant medium A and production medium I and incubating the production medium for about 66 hours.

B. Deacylation of N$_{Orn}$-t-BOC Complex

The A-21978C N$_{Orn}$-t-BOC complex (1185 g of crude substrate which contained about 176 g of A-21978C complex) was added to the fermentation medium. Deacylation was carried out as described in Preparation 1, Section B. Deacylation was complete, as indicated by HPLC, after about 24 hours.

C. Isolation of A-21978C N$_{Orn}$-t-BOC Nucleus

Fermentation broth (100 L.), obtained as described in Section B, was filtered with a filter aid (Hyflo Supercel). The filtrate was passed over a column containing 7.5 L. of HP-20 resin (DIAION); the column was washed with water (38 L.). Elution was monitored by silica gel/C$_{18}$ HPLC with UV detection at 254 nm. Some nucleus was eluted in the wash. Subsequent elution of nucleus was carried out with water:acetonitrile mixtures as follows: (95:5)-40 L.; (9:1)-40 L.; and (85:15)-100 L. Fractions containing the nucleus were combined, concentrated under vacuum to remove solvent, and freeze-dried to give 298.5 g of semi-purified A-21978C N$_{Orn}$-t-BOC nucleus.

D. Purification of A-21978C N$_{Orn}$-t-BOC Nucleus

Semi-purified A-21978C N$_{Orn}$-t-BOC nucleus (30 g), obtained as described in Section C, was dissolved in water:acetonitrile (9:1) containing 0.2% acetic acid and 0.8% pyridine (75 ml). This solution was applied to a 4.7×192-cm steel column containing 3.33 L. of silica gel (Quantum LP-1)/C$_{18}$ equilibrated in the same solvent system. The column was developed under pressure with water:acetonitrile:methanol (80:15:5) containing 0.2% acetic acid and 0.8% pyridine, collecting 350-ml fractions and detecting product by UV at 280 nm. Fractions containing the product were combined, concentrated under vacuum to remove solvent and freeze-dried to give 18.4 g of purified A-21978C N$_{Orn}$-t-BOC nucleus.

A-21978C N$_{Orn}$-t-BOC nucleus has the following characteristics:

(a) Form: white amorphous solid which fluoresces under short-wave UV (b) Empirical formula: C$_{67}$H$_{90}$N$_{16}$O$_{28}$ (c) Molecular weight: 1566

(d) Solubility: soluble in water (e) Infrared absorption spectrum (KBr disc) shows absorption maxima at:
3345 (broad), 3065 (weak), 2975 (weak), 2936 (weak), ~1710 (shoulder), 1660 (strong), 1530 (strong), 1452 (weak), 1395 (medium), 1368 (weak), 1341 (weak), 1250 (medium), 1228 (medium), 1166 (medium to weak) and 1063 (weak)

(f) UV absorption spectrum in 90% ethanol shows maxima at: 220 nm ($\epsilon$ 42,000) and 260 nm ($\epsilon$ 10,600)

(g) HPLC retention time = 6 min on 4.6-×300-mm silica-gel C$_{18}$ column, using H$_2$O/CH$_3$CN/CH$_3$OH (80:15:5) solvent containing 0.2% NH$_4$OAc at a flow rate of 2 ml/min with UV detection.

PREPARATION 5

Alternative Purification of A-21978C N$_{Orn}$-t-BOC Nucleus

Semi-purified A-21978C N$_{Orn}$-t-BOC nucleus (10.8 g), obtained as described in Preparation 4, Section C, was dissolved in water and applied to a column containing 80 ml of Amberlite IRA-68 (Rohm and Haas, Philadelphia, Pa., acetate cycle). The column was washed with water and, at a flow rate of 5 ml/min, was eluted sequentially with 0.05 N acetic acid (1080 ml), 0.1 N acetic acid (840 ml), and 0.2 N acetic acid (3120 ml), collecting 120-ml fractions. The column was monitored with analytical HPLC over silica gel/C$_{18}$, using a system of water:acetonitrile:methanol (80:15:5) containing 0.2% ammonium acetate and detecting product with UV at 254 nm. Fractions containing the product were combined; the pH of the solution was adjusted to 5.8 with pyridine; the resulting solution was concentrated under vacuum to a volume of about 200 ml. Water was added to the concentrate, and the resulting solution was reconcentrated to remove pyridine. This concentrate was freeze-dried to give 3.46 g of purified A-21978C N$_{Orn}$-t-BOC nucleus.

EXAMPLE 1

Preparation of N$_{Trp}$-p-(n-Dodecyloxy)benzoyl-N$_{Orn}$-t-BOC-A-21978C Nucleus A solution of 2,4,5-trichlorophenyl p-(n-dodecyloxy)benzoate (0.9 g), A-21978C t-BOC nucleus (0.9 g) in 400 ml of anhydrous dimethylformamide was allowed to stir at room temperature for 120 hours under an atmosphere of nitrogen. The solvent was removed by evaporation under reduced pressure. The residual material was stirred with a mixture of diethyl ether (400 ml) and chloroform (400 ml) for 2 hours. The product was separated by filtration and dried to give a light brown powder (0.962 g). A portion of this material (0.78 g) was dissolved in methanol (200 ml) and purified by preparative HPLC, using a "Prep LC/System 500" unit (Waters Associates, Inc., Milford MA) and a Prep Pak-500/C$_{18}$ Column (Waters Associates) as a stationary phase. The column was operated isocratically, using a water:methanol:acetonitrile (2:1:2) solvent system and collecting 250-ml fractions (1 fraction/min.). The desired compound was eluted in the 2nd to the 6th fractions.

Fractions were combined on the basis of TLC [reverse phase/C$_{18}$ silica gel, developed with water:methanol:acetonitrile (3:3:4), detected with Van Urk spray]. Bioautography of the combined fractions, using silica gel TLC, an acetonitrile:acetone:water (2:2:1) solvent, and *Staphylococcus aureus* as the detecting organism, indicated that the product was a single bioactive component. This procedure gave 0.421 g of N$_{Trp}$-p-(n-dodecyloxy)benzoyl-N$_{Orn}$-t-BOC-A-21978C nucleus.

EXAMPLE 2

Preparation of N$_{Trp}$-p-(n-dodecyloxy)benzoyl-A-21978C Nucleus

N$_{Trp}$-p-(n-Dodecyloxy)benzoyl-N$_{Orn}$-t-BOC-A-21978C nucleus (230 mg) was dissolved in 5 ml of trifluoroacetic acid containing 2% anisole and stirred for 5 minutes at 0° C. The solution was concentrated to an oil under vacuum, and the oil was triturated with Et$_2$O (100 ml). The solids were separated, air-dried, and taken up in water (10 ml). The pH of this solution was adjusted from 3.25 to 7 by the addition of pyridine. The resulting solution was lyophilized to give 179 mg of white amorphous N$_{Trp}$-p-(n-dodecyloxy)benzoyl-A-21978C nucleus. This compound has an R$_f$ value of about 0.78 on silica-gel TLC, using an acetonitrile:acetone:water (2:2:1) solvent system and Van Urk spray for detection.

EXAMPLE 3

The antibacterial activity of the compounds of formula 1 can be demonstrated in vitro. The results of the antibacterial testing of representative compounds of formula 1 using standard agar-plate disc-diffusion tests are set forth in Table I. In Table I activity is measured by the size (diameter in mm) of the observed zone in which growth of the microorganism is inhibited by the test compound.

TABLE I

Antibacterial Activity of Formula 1 Compounds by the Agar-Plate Disc-Diffusion Test

| Compound | | Size of Zone of Inhibition (mm)[a] | | | |
|---|---|---|---|---|---|
| R | $R^1$ | Staphylococcus aureus ATCC 6738P | Bacillus subtilis ATCC 6633 | Micrococcus luteus ATCC 9341 | B. subtilis ATCC 6633[b] |
| p-(n-dodecyloxy)benzoyl | H | 20 | 13 | 18 | 20 |
| p-(n-dodecyloxy)benzoyl | t-BOC | 20 | 10 | 15 | 22 |

[a]Compounds were suspended in water at a concentration of 1 mg/ml; a 7-mm disc was dipped into the suspension and then placed on the agar surface; incubation - 24–48 hours at 25–37° C.
[b]Grown on minimal nutrient agar In the agar-plate disc-diffusion tests summarized in Table I the compounds did not show activity against the following organisms at the levels tested:

Saccharomyces cerevisiae ATCC 2366, Neurospora crassa, Candida albicans, Trichophyton mentagrophytes, Proteus vulgaris ATCC 9484, Salmonella gallinarum, Escherichia coli ATCC 4157, Pseudomonas aeruginosa ATCC 9027, Serratia marcescens NRRL B284, or Pseudomonas solanacearum.

The results of the antibacterial testing of a representative compound of formula 1, using the standard agar-dilution test, are summarized in Table II. In Table II activity is measured by the minimal inhibitory concentration (MIC), i.e. the lowest concentration of compound which inhibits the growth of the microorganism.

TABLE II

Antibiotic Activity of $N_{Trp}$-p-(n-Dodecyloxy)benzoyl-A-21978C

| Test Organism | MIC Values[a] |
|---|---|
| Staphylococcus aureus X1.1 | 1 |
| Staphylococcus aureus V41[b] | 1 |
| Staphylococcus aureus X400[c] | 2 |
| Staphylococcus aureus S13E | 1 |
| Staphylococcus epidermidis EPI1 | 4 |
| Staphylococcus epidermidis EPI2 | 2 |
| Streptococcus pyogenes C203 | 0.25 |
| Streptococcus pneumoniae Park I | 0.015 |
| Streptococcus Group D X66 | 2 |
| Streptococcus Group 9960 | 1 |

[a]MIC in mcg/ml
[b]Pencillin-resistant strain
[c]Methicillin-resistant-strain

In the agar-dilution tests summarized in Table II the compound was not active at the levels tested against strains of the following organisms: Haemophilus influenzae, Shigella sonnei, Escherichia coli, Klebsiella pneumoniae, Enterobacter aerogenes, Enterobacter cloacae, Salmonella typhi, Pseudomonas aeruginosa, Serratia marcescens, Proteus morganii, Proteus inconstans, Proteus rettgeri, Citrobacter freundii and Bordetella bronchiseptica.

The representative A-21978C cyclic peptide of formula 1 has shown in vivo antimicrobial activity against experimental bacterial infections. When two doses of test compound were administered to mice in illustrative infections, the activity observed was measured as an $ED_{50}$ value [effective dose in mg/kg to protect fifty percent of the test animals: See Warren Wick, et al., J. Bacteriol. 81, 233–235 (1961)]. The $ED_{50}$ values observed are given in Table III.

TABLE III

In Vivo Activity of $N_{Trp}$-p-(n-Dodecyloxy)benzoyl-A-21978C

| | $ED_{50}$ Values[b] | |
|---|---|---|
| | Staphylococcus aureus | Streptococcus pyogenes |
| Formula 1 Compound[a] R | Subcutaneous | Subcutaneous | Oral |
| $N_{Trp}$—(p-(n-Dodecyloxy)benzoyl | 3.35 | 0.31 | >200 |

[a]$R^1$ = H
[b]mg/kg × 2

The acute toxicity of $N_{Trp}$-p-(n-dodecyloxy)benzoyl-A-21978C, when administered intravenously to mice and expressed as $LD_{50}$, was 67.5 mg/kg.

I claim:

1. An A-21978C cyclic peptide derivative of the formula:

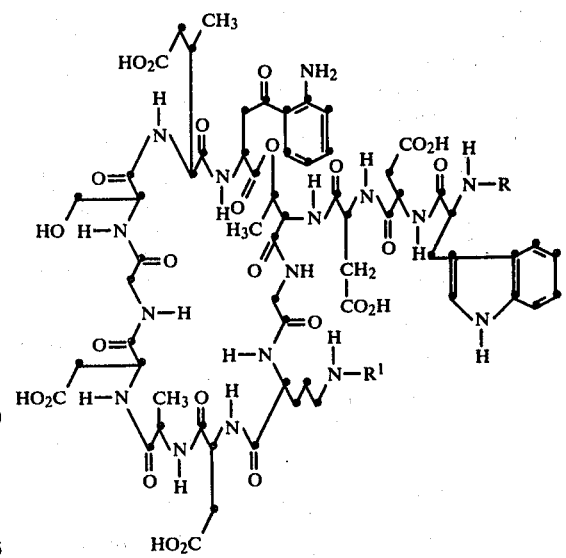

wherein R is a substituted benzoyl group of the formula

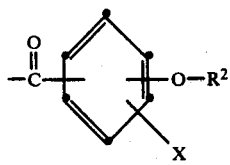

$R^2$ is $C_8$–$C_{15}$ alkyl; X is hydrogen, chloro, bromo, iodo, nitro, $C_1$–$C_3$ alkyl, hydroxy, $C_1$–$C_3$ alkoxy, or $C_1$–$C_3$ alkylthio; and $R^1$ is hydrogen or an amino-protecting group; and the salts thereof.

2. A compound of claim 1 wherein $R^2$ is $C_{10}$–$C_{13}$ alkyl and salts thereof.

3. A compound of claim 2 wherein $R^2$ is dodecyl and its salts.

4. A compound of claim 1, 2 or 3 wherein X is hydrogen and the salts thereof.

5. The compound of claim 2 wherein $R^2$ is p-(n-dodecyl) and X is hydrogen and its salts.

6. A compound of claim 1, 2 or 3 wherein X is selected from chloro, bromo, or iodo, and the salts thereof.

7. A compound of claim 1, 2, 3 or 5 wherein $R^1$ is an amino-protecting group and the salts thereof.

8. A compound of claim 7 wherein the amino-protecting group is tert-butoxycarbonyl and the salts thereof.

* * * * *